United States Patent [19]
Darnell et al.

[11] Patent Number: 4,486,389
[45] Date of Patent: Dec. 4, 1984

[54] FROZEN PLASMA THAWING SYSTEM

[75] Inventors: John W. Darnell, Waltham, Mass.; Roman Kuzyk, Hamilton Square, N.J.

[73] Assignee: Cryosan, Inc., Newton, Mass.

[21] Appl. No.: 392,641

[22] Filed: Jun. 28, 1982

[51] Int. Cl.³ ............................................. F28F 7/00
[52] U.S. Cl. ................................. 422/307; 165/46; 165/80 E; 422/25; 422/41
[58] Field of Search ..................... 422/25, 40, 41, 301, 422/99, 300, 307; 165/46, 80 R, 80 E, 104.19; 604/408; 248/95, 99

[56] References Cited

U.S. PATENT DOCUMENTS 2,061,427 11/1936 King ........................................ 165/46
2,914,445 11/1959 Clarke ............................. 165/104.19

OTHER PUBLICATIONS

Lab Oratory, Schaar and Company, Chicago, Ill., Sep. 1951, p. 9.

Primary Examiner—Barry Richman
Assistant Examiner—William R. Johnson
Attorney, Agent, or Firm—Wolf, Greenfield & Sacks

[57] ABSTRACT

A technique and apparatus for thawing a frozen blood plasma unit while maintaining the unit in a dry condition includes a water bath and a special holder which supports a thin plastic bag in which the plasma unit is contained. The holder maintains the bag and the plasma unit submerged in a manner which affords substantial thermal contact between the plasma unit and the water bath.

9 Claims, 7 Drawing Figures

FROZEN PLASMA THAWING SYSTEM

BACKGROUND AND SUMMARY OF THE INVENTION

This invention relates to improvements in thawing of blood plasma units. Storing blood plasma in a frozen state and then thawing it when needed is a common practice in blood banks of hospitals and the like. For many years the typical practice in the blood bank has been to select the required unit of plasma and simply place it into a controlled temperature water bath to thaw the unit to the liquid state. After thawing, the plasma unit is removed from the water bath and is temperature controlled for use anytime during the next twenty-four hours.

Plasma units typically are in the form of a sealed, prepackaged plastic pouch, holding 250 milliliters of plasma. The pouch includes one or more connector tubes through which the plasma may flow when the unit is in use. The connector tubes typically are presealed with a plastic membrane which is punctured when the unit is connected to the delivery cathether, as by a needle set inserted into the tube to puncture the membrane.

The foregoing practice of simply placing the blood plasma unit into a water bath has, in some instances, resulted in bacterial contamination of the plasma unit. Bacteria in the water bath may contact the plastic pouch in which the plasma is contained. While the plastic pouch itself provides a barrier against direct contamination of the plasma within the pouch, water from the bath sometimes seeps into contact with the inlet end of the connector tube. Should bacteria develop in or near the connector tube, the possibility exists that when the connector tube seal is punctured by the needle set to evacuate the plasma, the plasma may be contacted by the bacteria thereby contaminating the plasma. This type of difficulty has resulted in recent suggestions to use techniques designed to avoid contamination of the plasma container, and particularly contamination of the entry ports. The suggested technique has been to place the plasma, frozen in its pouch, within a polyethylene or other plastic bag, preferably a bag in which the seal is an hermetic seal such as a heat sealed or a self-sealing bag. The pouch, thus overwrapped and completely protected, is placed in the water bath to thaw the plasma within the inner plasma pouch. While this technique appears to be effective in avoiding contamination during the thawing process, it does present some additional difficulties. Among the difficulties is that because the bag is overwrapped within a sealed outer bag the time required to thaw the plasma unit necessarily is increased. Additionally, the bag tends to float on the water which further increases the thawing time. Moreover, this technique requires special heat sealing equipment or expensive bags with self-sealing features. Typically, such self-sealing or heat sealable bags are of the order of a minimum of 2 to 3 mils thick which provides an additional thermal barrier which further increases the thawing time.

The present invention provides a technique and system which achieves thawing in a water bath, while maintaining the plasma bag in a dry, contaminant-free configuration, but in a manner which avoids foregoing difficulties. In accordance with the present invention, the frozen plasma unit is placed within a thin, open-topped plastic bag. The bag then is placed in a special holder associated with the water bath. The holder and the bag cooperate to maintain the plasma unit, which is within the lower end of the thin plastic bag, well submerged below the surface of the water. The thin, open topped plastic bag conforms closely to the shape and configuration of the frozen plasma container thereby avoiding any substantial insulative spaces which might retard the thawing process. The holder and water bath are specially constructed to facilitate easy attachment and detachment of the bag from the holder. After the thawing process has been completed, the plastic bag can be removed in its entirety and the still dry, thawed plasma unit may be removed with assurance that it has not been contaminated by bacteria as a result of contact with the thawing bath.

It is among the objects of the invention to provide an improved system for thawing frozen plasma units.

A further object of the invention is to provide an improved system for thawing frozen plasma samples which maintains the plasma sample in a dry condition while exposing it to the thawing heat from a fluid bath.

Another object of the invention is to provide a system of the type in which the thawing time is not materially increased.

A further object of the invention is to provide improved, yet simplified apparatus for practicing the invention.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 4:
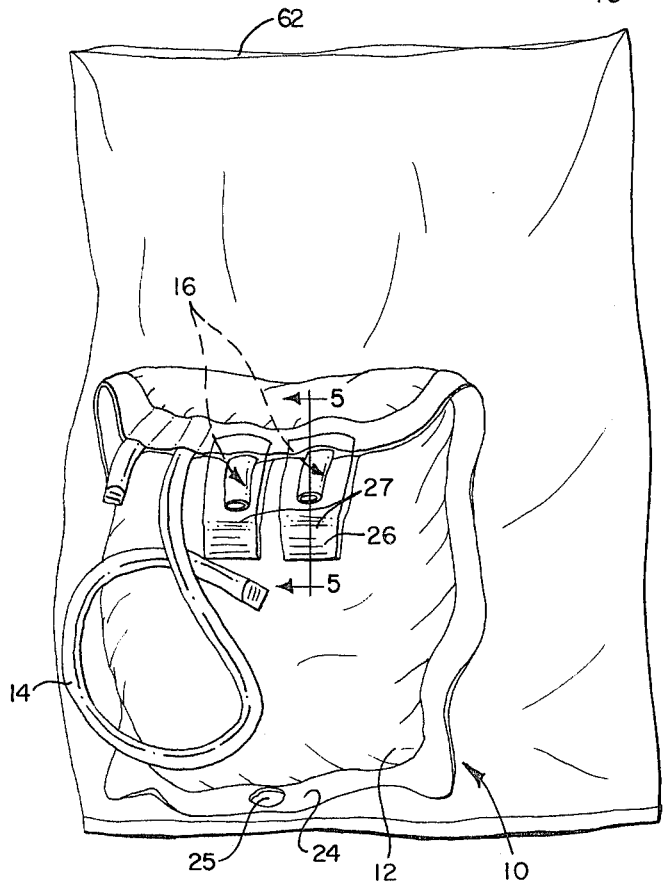
FIG. 4 is an illustration of a frozen plasma unit pouch within the open topped plastic bag before insertion into the thaw bath.
Figure 5:
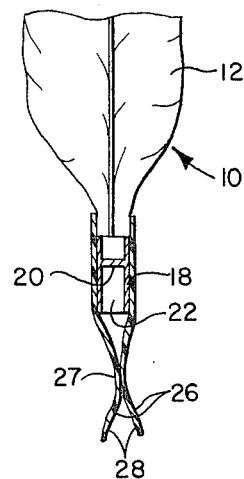
FIG. 5 is a side elevation, partly in section, of a portion of the plasma unit pouch, after thawing and illustrating the connector tube of the pouch, as seen along the line 5—5 of FIG. 4.

FIG. 4 shows a typical plasma unit indicated generally at the reference character 10 which includes a relatively thick plastic pouch-like container 12 filled with the plasma. The pouch 12 typically will have at least one filling port 14 which will be sealed and which will have been used in filling the pouch as well as one, or sometimes two outlet ports 16 through which the plasma will flow after being thawed when the unit is used. The outlet port 16 typically includes an integral elongated connector tube 18 which is in communication with the interior of the plastic container 12 (see FIG. 5). The connector tube 18 typically is sealed at a location intermediate its ends by an integral plastic membrane 20 which is puncturable by the spike of an administration set. The connector tube defines a socket 22 receptive to a connector of a catheter which has an integral spike to puncture the membrane 20. The other end of the plastic plasma container 12 is typically provided with a flange 24 having a hole 25 to enable the unit to be suspended overhead when administering the plasma to a patient. It is a commonly accepted practice to try to maintain the outlet ports 16 and connector tube 18 in a completely sealed isolated environment so as to avoid contamination during the thawing process and until the moment at which the unit is to be used. To that end, it is common practice to form integral sealing flaps 26 which extend about the protruding end of the outlet port 16 and connector tube 18. The sealing flaps 26 are heat sealed to each other along line 27 to completely isolate the outlet port 16 and connector tube 18. The outer ends 28 of the sealing flaps are separable and provide a convenient grippable means by which the sealing flaps may be pulled apart to expose the connector tube 18 at the moment of use.

The technique for providing the sealing flaps 26 has been found to be less than completely satisfactory. If the sealing flaps 26 become wet, bacterially contaminated water may be transmitted from the flaps to the connector tube 18 when the flaps are separated to expose the connector tube.

For the foregoing reasons, as mentioned above, it has become a recent practice to thaw the plasma unit 10 by placing it in a sealed thawing bag, such as a sealed plastic bag and immersing that wrapped configuration in the thawing bath. As mentioned above, that creates air pockets which tend to decrease the rate of heat transferred and also tend to further enhance the floating characteristic of the overwrapped unit 10, both of which slow down the thawing process.

In accordance with the present invention, the plasma unit is placed in a thin plastic bag having an open, unsealed top. The bag may be formed from very thin polyethylene, preferably of the order of about 1 mil thickness. The thin bag tends to conform closely to the contours of the frozen plasma pouch 12 due to the pressure of being held submerged underwater and provides a relatively thin layer which does not materially interfere with heat transfer during the thawing process. Thus, the plasma unit 10 simply is placed in the bottom of such a thawing bag 30 and the thawing bag, with contained plasma unit 10 then is placed into the water bath 32 and is held in the water bath by the pouch holder indicated generally at 34.

The water bath may take any of a number of forms and preferably includes a tub 36 through which thermostatically controlled water is circulated. To that end, the tub may be associated with a pump, a heating element and thermostat controls, indicated generally as being contained within a housing 38 associated with the tub 36. The details of such pump and control mechanisms are well known to those skilled in the art and require no further discussion. The tub 36 may be mounted for rocking or pivotal movement and may be connected to an oscillating mechanism (not shown) to agitate the water in addition to circulating it, thereby to promote uniform bath temperature throughout the tub.

In accordance with the present invention a bag holder is provided to maintain the lower end of the bag (which contains the plasma pouch) below the water level of the bath while simultaneously holding the upper open end of the bag exposed to the atmosphere and other communication with the water. As shown in the illustrated embodiment of FIGS. 1-3 the holder includes an upper wall 40 and a parallel lower wall 42. Each of the upper and lower walls is provided with a plurality of slots 44, 46 respectively. The lower wall is connected to and suspended from the upper wall by a pair of side walls 48 and additional reinforcing members 50 may be connected between the upper and lower walls 40, 42 as shown. The upper wall 40 is longer than the lower wall 42 so that the outer ends of the upper wall 40 extend outwardly beyond the side walls 48. The ends of the upper walls provide a convenient means by which the device may be mounted to the tub 36. In the embodiment shown, the outer ends of the upper wall 40 may be provided with openings 52 to receive registration pins 54 which may be secured to and extend upwardly from the tub 36. In the embodiment, the mounting means for the pouch holder 34 preferably is arranged to provide a substantial space 56 between a wall 58 of the tub and the slotted side of the upper and lower wall 40, 42. The space 56 should be adequate for the user to insert and remove the bags from the holder with ease.

The slots 44, 46 preferably are arranged in pairs so that each slot 44 and the upper wall is provided with a corresponding slot 46 in the lower wall. The parts of the bag holder 34 are constructed and arranged so that the lower wall 42 will remain submerged or in close proximity to the surface of the water.

Figure 1:
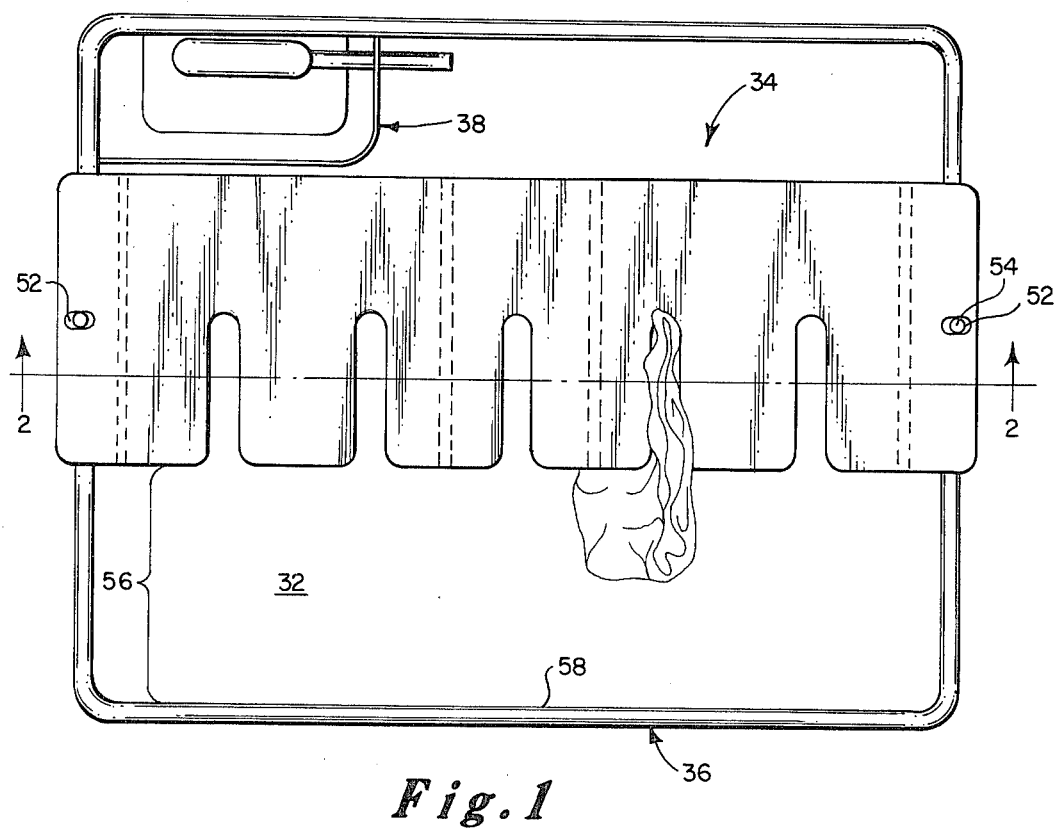
FIG. 1 is a plan view of one embodiment of the invention illustrating the water bath bag holder and bag.
Figure 2:
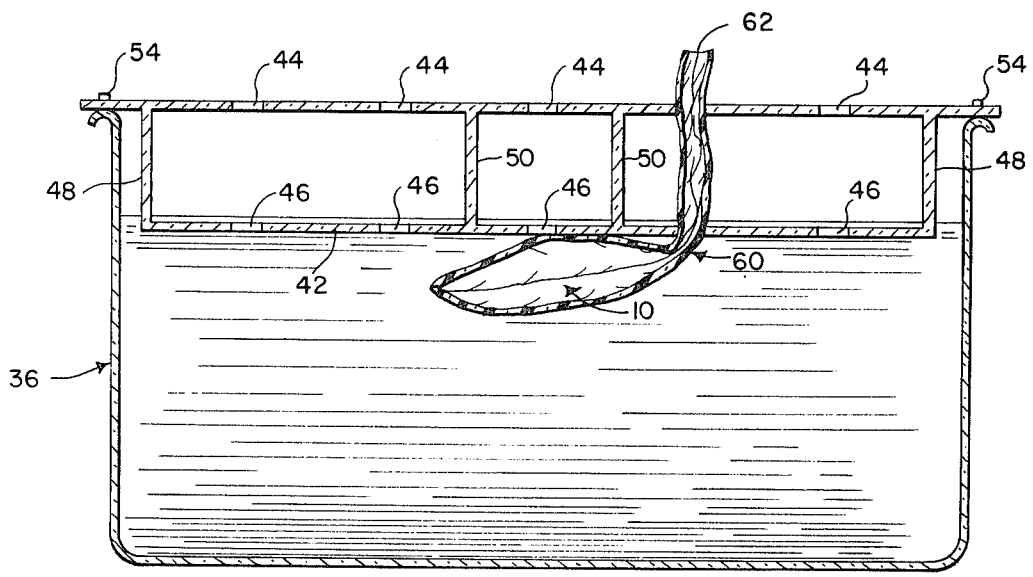
FIG. 2 is an illustration of the system of FIG. 1 as seen along the line 2—2 and showing the plasma unit within the bag as submerged.
Figure 3:
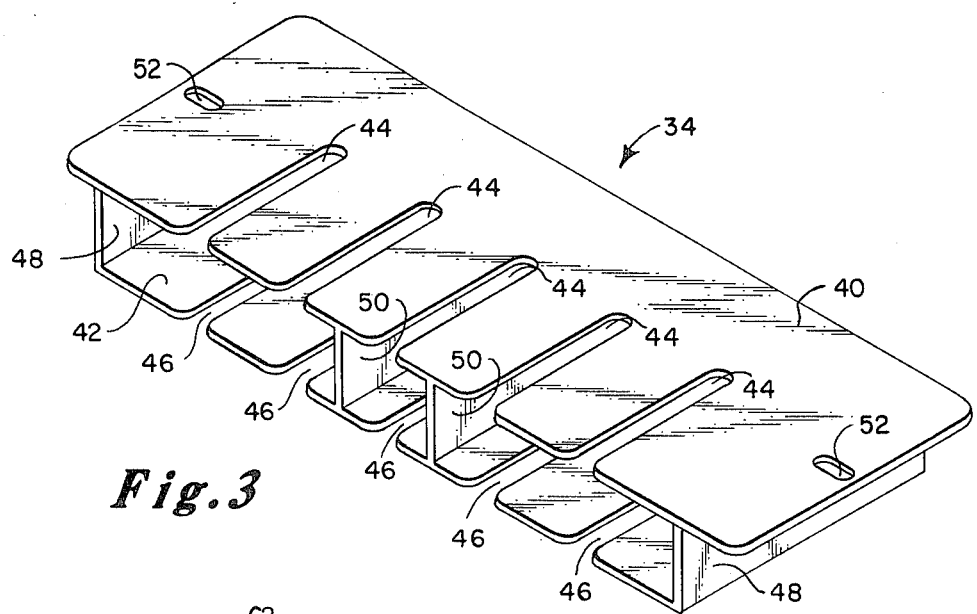
FIG. 3 is an isometric view of the holder shown in FIGS. 1 and 2.

The system shown in FIGS. 1-4 is used by inserting the frozen plasma unit 10 into the thin open ended, unsealed plastic bag (as shown in FIG. 4). With the plasma unit at the bottom of the bag 60, the pouch is then inserted into the bath, with its lower end containing the frozen plasma unit beneath the lower wall 42. The bag 60 is advanced into a pair of upper and lower slots as shown in FIG. 1. The pair of slots, 44, 46 assure that the upper end 62 of the open bag 60 will remain exposed to the atmosphere and at a location well above the water level so as not to be contaminated with any of the water. The plasma unit 10 which is frozen and is buoyant, will be maintained fully submerged by the lower wall 42 of the holder 34.

In accordance with the present invention, the thin plastic bag 60 self-conforms to the contour and shape of the frozen plasma pouch 12. This results from a combination of factors including the relatively thin configuration of the bag plastic as well as the continued exposure of the interior of the bag to the atmosphere, through the upper open end of the bag. As will be appreciated from the foregoing, when the plasma unit, within the bottom of the thin, flexible vented bag is submerged, the pressure of the water about the submerged plasma unit will cause the lower end of the bag to conform closely to and press against the outside contour and configuration of the plastic pouch 12 of the plasma unit. The creation of air spaces tending to reduce thermal conductivity thereby is avoided.

Figure 6:
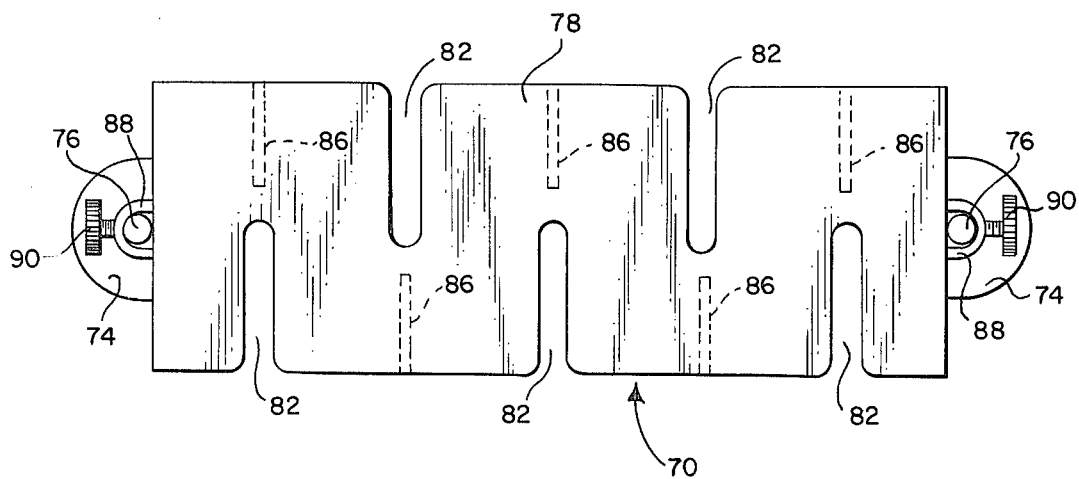
FIGS. 6 and 7 are illustrations of another embodiment of the holder utilizing the present invention.
Figure 7:
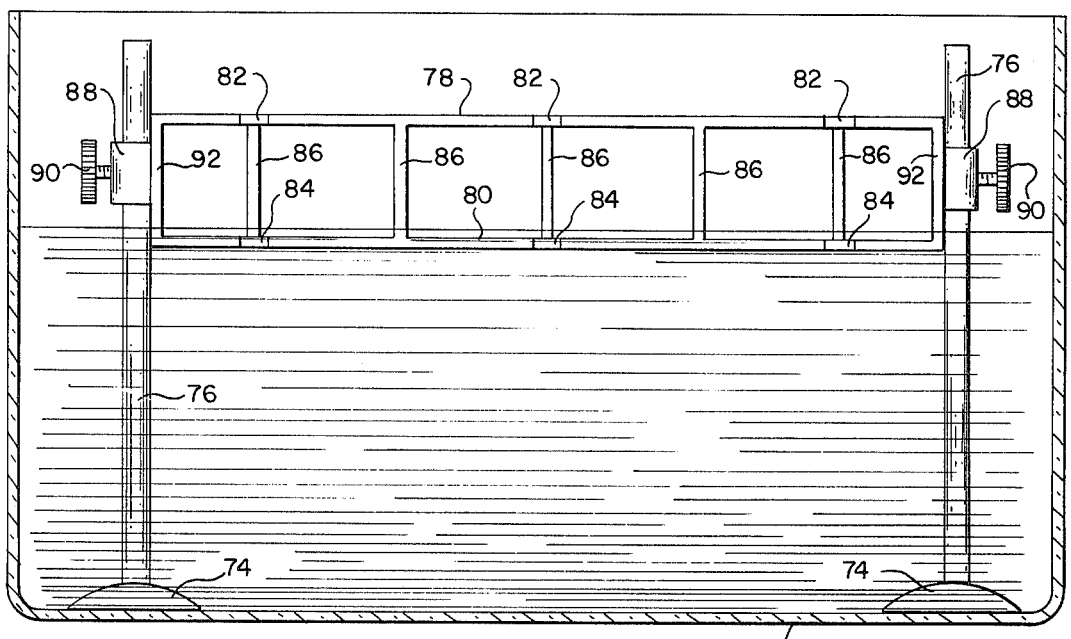

The foregoing illustrates but one of various possible configurations of holders utilizing the present system. FIGS. 6 and 7 illustrate still another embodiment of a bag holder indicated generally at 70. In this embodiment the device may be mounted directly to the bottom wall 72 of a tub as by suction cups 74. The suction cups support upwardly extending rods 76. The rods, in turn, carry a pair of walls including an upper wall 78 and a lower wall 80 which correspond and function similarly to the upper and lower walls 40, 42 of the previously described embodiment. In this embodiment, each of the upper and lower walls 78, 80 is provided with a plurality of slots arranged at opposite alternating sides of the wall. The slots 82, 84 may be arranged in pairs and similar fashion to those in the previously described embodiment. The upper and lower walls 78, 80 may be secured together by reinforcing members 86 which also serve to provide sufficient spacing for the upper and lower walls.

The holder 70 in this embodiment preferably is mounted for vertical adjustable movement with respect to the rods 76 as by guides 88 and associated thumb screws 90. The guides 88 may be secured to the end walls 92 of the device. With this configuration the device may be raised and lowered to adjust to the water level of the particular bath thereby enabling the device to be used with substantially any bath.

In connection with each of the foregoing embodiments, the width of the slots should be such to permit free air flow through the bag to enable the bag to conform closely to the shape and contour of the plasma unit 10 while frozen and at all stages of thawing. In most instances it will be feasible to place two bags in each pair of slots which in the illustrated embodiments of the invention that would enable ten plasma units to be thawed at the same time.

From the foregoing it will be understood that the principles of the invention include a means for supporting a thin flexible pouch which is capable of conforming easily to the contour of the plasma bag in a manner in which the open upper end of the pouch is maintained well above the water level and in communication with the atmosphere. The supporting means is also constructed so as to maintain the lower end of the pouch which contains the frozen plasma unit well below the water level to maintain it in a submerged configuration.

It should be understood that the foregoing description of the invention is intended merely to be illustrative thereof and that other modifications and embodiments may be apparent to those skilled in the art without departing from its spirit.

Having thus described the invention what I desire to claim and secure by Letters Patent is:

1. A system for thawing frozen plasma units comprising a water bath;
    a thin, flexible, waterproof pouch having a portion vented to the atmosphere, the pouch being receptive to a frozen plasma unit;
    means for supporting the pouch within the water bath so that the lower end of the pouch when containing a plasma unit, is maintained in a substantially submerged position while the vented portion of the pouch is maintained in spaced relation from the water level of the bath and in communication with the atmosphere;
    said pouch being sufficiently flexible as to be capable of conforming into intimate contact with a plasma unit contained therein under the influence of the pressure of the water in which the pouch is submerged,
    whereby a frozen plasma unit may be thawed rapidly and uniformly while maintained in a dry condition.

2. A system as defined in claim 1 wherein the flexible pouch is polyethylene having a thickness of not substantially greater than 1 mil.

3. A system as defined in claim 1 wherein the means to support the bag comprises:
    a pouch holder having a top wall and a lower wall, spaced below the top wall, each of the top wall and lower wall having at least one slot therein to form at least one pouch receiving slot pair;
    means for supporting the holder so that its lower wall is substantially at or below the water level of the water bath.

4. A device as defined in claim 3 further comprising means for adjustably positioning the height of the holder.

5. A system as defined in claim 3 wherein each of the top and lower walls is provided with a plurality of slots extending along one edge of each wall, the slots being arranged in pairs, in which each pair includes an upper and a lower slot.

6. A system as defined in claim 3 wherein the holder further comprises:
    each of the top and lower walls includes slots formed alternately on opposite edges of the respective wall facing in alternately different directions.

7. A system as defined in claim 3 further comprising:
    the water bath including a tub having sidewalls;
    the pouch holder being located with respect to one of the sidewalls of the tub so that there is a substantial space between said sidewall and said holder, said substantial space providing a region to facilitate insertion and removal of the pouches from said at least one slot pair and from the system.

8. A system as defined in claim 7 wherein the holder further comprises:
    the top wall being longer than the bottom wall and defining laterally extending flanges, the flanges being adapted to rest on the upper edge of the sidewall of the water bath tub.

9. A system as defined in claim 8 further comprising:
    the lateral flanges of the holder being provided with slots adapted to receive upwardly extending registration pins mounted to the sidewalls of the bath tub.

* * * * *